United States Patent [19]

Sonderegger

[11] Patent Number: 5,413,203

[45] Date of Patent: May 9, 1995

[54] METHODS AND APPARATUS FOR TRANSPORTING AND POSITIONING MICRO-MECHANICAL PARTS

[75] Inventor: Marcel Sonderegger, Schaffhausen, Switzerland

[73] Assignee: United States Surgical Corporation, Norwalk, Conn.

[21] Appl. No.: 140,355

[22] Filed: Oct. 20, 1993

[30] Foreign Application Priority Data

Mar. 11, 1993 [DE] Germany ............... 43 07 730.7

[51] Int. Cl.$^6$ ............................................ B65G 19/00
[52] U.S. Cl. .................................. 198/345.1; 198/619; 198/721
[58] Field of Search ............ 198/380, 619, 721, 345.1; 406/86, 87; 269/20

[56] References Cited

U.S. PATENT DOCUMENTS 4,591,392  5/1986  Beck .

FOREIGN PATENT DOCUMENTS

| 115733 | 1/1930 | Australia . |
| 1510297 | 1/1968 | France . |
| 1756045 | 8/1970 | Germany . |
| 61-81324 | 8/1986 | Japan . |

*Primary Examiner*—D. Glenn Dayoan

[57] ABSTRACT

A process and apparatus for transporting micro-mechanical parts, for example surgical needles, on a liquid surface by holding the parts on the liquid surface on account of the surface tension of the liquid, such that a predetermined path is formed and subjecting the parts to an external force thereby transporting the parts along the predetermined path.

32 Claims, 8 Drawing Sheets

METHODS AND APPARATUS FOR TRANSPORTING AND POSITIONING MICRO-MECHANICAL PARTS

BACKGROUND OF THE INVENTION

The invention relates to methods and apparatus for transporting and positioning micro-mechanical parts.

In terms of micro-mechanical parts, preformed parts are to be understood, and therefore not naturally occurring parts. The term "micro-mechanical part" includes both "oblong" as well as "planar" parts. In respect of oblong micro-mechanical parts, such manufactured parts are to be understood which have a cross-sectional dimension in the order of micrometers or millimeters, but the longitudinal dimensions thereof can be desirably longer. Such oblong micro-mechanical parts can, for example, be micro-surgical needles, threads or wires. The cross section of such manufactured parts can be circular, elliptical, oval, rectangular, triangular or polygonal and also have any desired open or hollow geometries. The cross section can also vary as appropriate along the longitudinal length of the part. In respect of planar micro-mechanical parts, such manufactured parts are to be understood which are substantially planar, namely plate- or disc-shaped, for example. Their thickness dimensions are in the order of micrometers or millimeters, while the length and width dimensions can be substantially greater. The planar micro-mechanical parts can have the most varying surface and edge contours. The micro-mechanical parts can be metallic or parts consisting of plastics or of natural materials such as, for example, natural textile fibers.

Up to now, during the individual processing steps within a production and packaging process, micro-mechanical parts are either transported and positioned by means of a mechanical gripper or handled manually, for example, by means of a pincer. In the case of manual handling, the transport or positioning of micro-mechanical parts previously required the use of microscopes and, in the case of machine handling, the use of very complex mechanical and optical systems. The main problem with current handling methods consists in that the micro-mechanical parts are mechanically gripped and can be easily damaged as the thickness of, for example, a micro-surgical needle can be only 70 μm, for example. As the handling forces are often very large, very slight but undesirable plastic deformation of the manufactured part can occur.

Furthermore, positioning of a micro-mechanical part in the micrometer range is particularly difficult, as the moving mechanical gripper means must be precisely positioned with respect to a micro-mechanical part. In previous handling methods, the problem also exists that the adhesion force between the manufactured part and the tool must be overcome. As soon as the micro-mechanical part has made contact with the tool, a relatively large force is necessary in order to displace it on the tool or to remove it from this again.

SUMMARY OF THE INVENTION

It is therefore the object of the invention to provide a simple and safe process and apparatus for transporting and positioning micro-mechanical parts.

On account of the invention, a completely new type of process for transporting and positioning micro-mechanical parts is provided. The invention makes use of the fact that micro-mechanical parts as have been described above, namely parts with a substantially oblong shape which have a very small cross sectional dimension, or parts with a substantially planar shape which have a very thin dimension of thickness, can be carried on the surface of a liquid by the surface tension. Thus, micro-mechanical parts which are specifically heavier than liquid are transported and positioned on the surface of a liquid. The invention therefore relates to micro-mechanical parts of the type described above which are substantially or exclusively held on a liquid surface on account of the surface tension. For example, a steel wire with a diameter of up to approx. 0.3 mm is carried by the surface tension, independently of its length. In particular, micro-surgical needles, threads and comparable manufactured parts are held on the liquid surface on account of the surface tension. Additionally, a liquid surface also carries thin metallic plates, foils or lamellas which can also be extended in length and width.

BRIEF DESCRIPTION OF THE FIGURES

FIG. 1b shows a longitudinal cross-sectional view (Ib—Ib) of the channel according to FIG. 1a;

FIG. 1c shows a cross-sectional view (Ic—Ic) of the channel according to FIG. 1a;

DESCRIPTION OF THE PREFERRED EMBODIMENTS

In the inventive process for transporting micro-mechanical parts, the micro-mechanical part is first placed on the surface of a still liquid and held there on account of the surface tension. The placing of the micro-mechanical part on the liquid surface ensues, for example, by allowing this to fall from a relatively low height. A predetermined path is formed along which the micro-mechanical part is transported on the surface of the liquid by means of external forces to which the micro-mechanical part is subjected. In this process, the micro-mechanical part is protected on the liquid surface from damage or deformation by the liquid surrounding it. Furthermore, as only a very small frictional resistance occurs on the liquid surface, only very small external forces are required to move the part along the predetermined path. Preferably, the micro-mechanical part is transported on the liquid surface by means of electromagnetic forces, gravitational forces or by means of aerodynamic forces. Contrary to the holding and transporting of a micro-mechanical part with the usual mechanical gripper means, the micro-mechanical part in the inventive process is only subjected to very small forces by means of which it is neither damaged nor plastically deformed. The inventive process therefore represents a very simple, cost effective and, simultaneously, very safe transport method.

A preferred embodiment of an apparatus for carrying out the inventive process for transporting oblong micro-mechanical parts as previously described consists of a channel, the channel walls of which are wetted by a liquid, a channel width which is greater than the width of the micro-mechanical part, and such a channel cross sectional geometry and such a quantity of liquid in the channel that, before placement of the micro-mechanical part, and on account of adhesion and cohesion forces between the liquid, the channel walls and the medium above the liquid, the liquid surface is formed such that it is concavely curved in the direction of the channel transverse cross section and a predetermined trough-shaped path for the micro-mechanical part ensues, and consists of means in order to purposefully subject the micro-mechanical part to external forces. On account of the concave curvature of the liquid surface in the direction of the channel cross section, a "transport trough" is formed along which micro-mechanical part is conveyed. An oblong micro-mechanical part placed on the liquid surface in the channel aligns itself under the influence of gravitational force so that it lies at the lowest point of the curved liquid surface and with its longitudinal axis parallel to the longitudinal axis of the channel walls. On account of the curved liquid surface, it is therefore prevented that the micro-mechanical part strikes against the channel walls during transport and, simultaneously, a defined alignment of the part in the channel is achieved. The longitudinal axis of the micro-mechanical part is set in parallel to the predetermined path. In this embodiment, the path is geometrically predetermined by the form of the liquid surface. Following placement of the micro-mechanical part on the liquid surface which is concavely curved transversely to the transport direction, the liquid surface is convexly curved adjacent the part and the curvature then changes after a turning point in the direction towards the channel walls into a concave curvature. On account of the tendency of the liquid to minimize the liquid surface, the part assumes a stable position at the lowest point of the curved path. In a symmetrical channel cross section, the micro-mechanical part is in the centre of the channel. The surrounding atmosphere normally acts as the medium above the liquid surface, but it is also possible to use a different gas or a second liquid as a medium above the channel which does not mix with the liquid in the channel.

The above described exemplified embodiment is suitable for oblong micro-mechanical parts as well as for micro-mechanical parts having a width which still permits the liquid surface in a channel, by the appropriate selection of the channel geometry, the surface of the channel walls as well as the quantity of liquid wetting the channel, to form in the channel direction as a concavely curved surface.

For planar micro-mechanical parts, the width of which is so great that a continuous concave surface curvature of the liquid can no longer be realized in the channel cross section, a further embodiment is preferred in which the liquid surface is concavely curved at the channel edges and flat in the center of the channel, in the direction of the channel cross section, prior to placement of the micro-mechanical part. In this case, the channel width is to be provided with a dimension only so much greater than the width of the micro-mechanical part that the part assumes a stable position within the channel in the channel cross section. Following placement of the part on the liquid surface, a surface curvature is formed which begins convexly beside the micro-mechanical part in the transverse direction of the channel and, after a turning point, is concave approaching the channel wall. Otherwise, this embodiment corresponds to the previously described embodiment.

In further preferred embodiments of apparatus for carrying out the inventive process for transporting micro-mechanical parts, a basin filled with liquid is provided having boundary members arranged at a distance from one another which bound at least one transport lane on the liquid surface, the width of the transport lane being greater than the width of the micro-mechanical part and this width being selected in such a manner and the geometry of the edges bounding the transport lane being formed such that, before placement of the small micro-mechanical part, and on account of the adhesion and cohesion forces between the liquid, the edges of the boundary membery and the medium above the liquid, the surface of the liquid adjusts such that a curved predetermined path for the micro-mechanical part ensues in the direction of the channel cross section, and means are provided in order to purposefully subject the micro-mechanical part to external forces. In this case, in an embodiment which is suitable for substantially oblong micro-mechanical parts, the liquid surface is concavely curved in the cross-sectional direction of the channel, and, in another embodiment suitable for planar micro-mechanical parts, the liquid surface is concavely curved in the direction of the channel cross-section at the channel edges, and flat in the center of the channel. The shape of the channel surface in both of these embodiments is analogous to the previously described embodiments with a channel. On account of the boundary members, which are preferably plate-shaped members, several transport lanes can be defined in one basin on the liquid surface. These can extend separately or also be connected to one another.

In all of the four previously described embodiments of apparatus for carrying out the inventive transport process, it is advantageous to form the means by which the micro-mechanical part is purposefully subjected to external forces as a synchronous linear motor. In this case, it is favourable to range the stator of the synchronous linear motor adjacent the predetermined path of the micro-mechanical part in such a manner that the stator follows the predetermined path with its longitudinal extension. The rotor of the synchronous linear motor is in this case formed by the micro-mechanical part on the liquid surface in the channel or in the transport lane electromagnetic forces are exerted on the micro-mechanical part by means of the synchronous linear motor to transport it along the predetermined path in the channel or in the transport lane. As already explained, the path for the micro-mechanical part is geometrically predetermined by the extension of the channel or the transport lane and the curvature of the liquid surface transversely to the channel or the transport lane. On account of the electromagnetic field of the linear motor, an external force is then exerted on the micro-mechanical part which "pushes" the part on the liquid surface in the transport direction along the channel or the transport lane. On account of the very low frictional resistance on the liquid surface, only a small transport force is necessary. It is useful to premagnetize the micro-mechanical part acting as the rotor. The stator is suitably arranged beneath the predetermined path. The stator can, for example, be arranged in the liquid of the basin or in the base of the basin or in the base of the channel. Furthermore, an arrangement of the stator above the predetermined path or to the side thereof is possible. On account of the described linear motor, the external forces for transporting the part is applied in an advantageous manner without any mechanical contact.

Instead of using a synchronous linear motor as means for subjecting the micro-mechanical part to external forces, it is equally possible to use an airstream generator. For example, nossles mounted along the predetermined path of the micro-mechanical part can purposefully blow airstreams onto the part so that it is moved in the transport direction along the channel or the transport lane.

Both in the case of movement of the micro-mechanical part by a linear motor or by means of an airstream generator, transporting of manufactured parts is possible over desirably long distances without problems.

For transporting over short distances, a further preferred embodiment is suitable for carrying out the inventive transport process for the micro-mechanical part. In this embodiment, a channel is provided, the channel walls of which are wetted by a liquid and which channel has a channel width that is greater than the width of the small micro-mechanical part and has such a channel cross-sectional geometry and such an amount of liquid in the channel that, before placement of the micro-mechanical part, and on account of adhesion and cohesion forces between the liquid, the channel walls and the medium above the liquid, the channel surface is formed such that it is concavely curved in the direction of the channel cross-section and a predetermined trough-shaped path for the micro-mechanical part ensues, and wherein the channel width increases along the predetermined path in the transport direction. On account of a such a change in the channel width or the channel shape, gradients in the liquid surface are obtained. On account of the widening of the channel along the transport direction, the curvature of the liquid surface changes along the widening in such a manner that a gradient results along the transport direction. A driving force due to the incline then acts in the section of the gradient-drop as a force component of gravitational force on the micro-mechanical part to be transported and this is correspondingly accelerated. For short distances, one therefore obtains an adequate transport system for micro-mechanical parts and, on account of the low frictional resistance on the liquid surface, practically the entire potential energy of the micro-mechanical part is converted into kinetic energy. This purposeful utilization of gravitation subjects the micromechanical part to a transport force without a mechanical contact being necessary.

In a further useful embodiment of an apparatus for carrying out the inventive transport process for a micro-mechanical part, a basin filled with liquid with a flat liquid surface and a synchronous linear motor are provided, the stator of the synchronous linear motor being arranged parallel to the liquid surface, the section of the path of the micro-mechanical part on the liquid surface above the stator being predetermined on account of its extension in the longitudinal direction, and the rotor of the synchronous linear motor respectively being formed by a micro-mechanical part placed in the basin on the liquid surface. Preferably, the stator is arranged beneath the liquid. It can, however, also be arranged in the liquid. In an arrangement of the stator beneath the liquid, the electrics and liquid are advantageously separated from one another. In this exemplified embodiment, the path of the micro-mechanical part is predetermined by the extension of the stator of the synchronous linear motor. In contrast to the previously described embodiments, the liquid surface is not "bent" by utilizing capillary forces, but rather, the micro-mechanical part is transported on a flat liquid surface. However, other than in the previous embodiments, the micromechanical part is not stabilized in terms of its alignment on the liquid surface when the electric current is interrupted.

In the inventive process for positioning a micro-mechanical part, a micro-mechanical part is placed on a liquid surface and held there on account of the surface tension, the geometry of this liquid surface being formed such that the micro-mechanical part is definitively aligned in terms of its spatial orientation, and means are provided by which the spatial position of the micro-mechanical part can be definitively set.

In a preferred embodiment of an apparatus for carrying out the inventive positioning process, a channel section is provided which is limited in its longitudinal dimension by means of two channel end walls, the proportions of which substantially correspond to the proportions of the small micro-mechanical part to be positioned, and the geometrical dimensions of the channel section are only slightly greater than the dimensions of the micro-mechanical part, wherein the channel section includes such an amount of liquid that the liquid surface is concavely curved on account of adhesion and cohesion forces between the liquid, the channel walls and the medium above the liquid. This exemplified embodiment corresponds to the previously described channel for carrying out the transport process, but the channel walls in this case form a means by which the spatial position of the micro-mechanical part is fixed. Without the channel walls, and analogous to the alignment of the micro-mechanical part in the transport channel, the micro-mechanical part is definitively orientated in terms of its spatial angular position, namely with its longitudinal axis parallel to the channel side walls. However, as the micro-mechanical part is displaceable in the transport channel along the transpor path, the two channel end walls are provided in order to define the spatial position, namely the path position of the micro-mechanical part. According to this process, both the angular position as well as the spatial position of the micro-mechanical part are fixed. The liquid surface of the channel section is concavely curved and a micro-mechanical part placed on the liquid surface adopts a stable position on the concave liquid surface on account of the influence of gravitiy. Following placement of the micro-mechanical part, the liquid surface bends about the part firstly concavely and then changes towards the channel walls via a turning point to have a concave curvature. In this case the liquid tends to minimize the surface so that the placed part adopts a stable position. This embodiment is suitable for positiong micromechanical parts. In a further exemplified embodiment for substantially planar micro-mechanical parts, a corresponding channel section is provided, the liquid surface of which is only concavely curved at the channel walls and is flat in the center of the channel section. In this case, the dimensions of the channel section are only slightly greater than the dimensions of the part to be positioned so that the part is stably positioned within the channel section on account of the curvature of the liquid surface in the vicinity of the channel walls.

In further exemplified embodiments of apparatus for carrying out the inventive positioning process, a boundary member is arranged on the surface of liquid in a basin filled with the liquid and bounds an area on the liquid surface, wherein the proportions of the area substantially correspond to those of the small micro-mechanical part to be positioned, and the geometric dimensions of the area are only slightly greater than those of the small micro-mechanical part, and wherein the edges of the boundary member are shaped in such a manner that, before placement of the small micro-mechanical part, and on account of adhesion and cohesion forces between the liquid, the edges of the boundary member and the medium above the liquid, the liquid surface is formed such that it is concavely curved. In addition to this embodiment for oblong micro-mechanical parts, a corresponding embodiment is advantageous for planar parts in which the liquid surface is concavely curved along the edges of the boundary member and flat in the middle of the area. The boundary member can, for example, be plate-shaped, and several areas can also be provided for simultaneously positioning several micro-mechanical parts in the boundary member.

As already described in connection with the apparatus for carrying out the inventive transport process, other than the surrounding atmosphere, the medium above the liquid can also be another gas or a second liquid which does not mix with the first liquid. In the described exemplified embodiments of apparatus for carrying out the positioning process, the micro-mechanical part is placed, for example, by being dropped from a low height on to the liquid surface and then independently maintains a predetermined stable position in the channel section or in the bounded area. This provides a simple and safe process for positioning micro-mechanical parts. The problems which occur in the case of usual positioning processes on account of adhesion forces between the manufactured part and the tool therefore do not arise. Additionally, there is no danger of the part being damaged or plastically deformed when being positioned, as the micro-mechanical part positions itself on the liquid surface.

In a further exemplified embodiment of an apparatus for carrying out the inventive positioning process, a channel is provided, the walls of the channel being wetted with a liquid, and the channel has a channel width which is greater than the width of the micromechanical part, and such a channel cross-sectional geometry and such an amount of liquid in the channel that, before placement of the micro-mechanical part, and on account of adhesion and cohesion forces between the liquid, the channel walls and the medium above the liquid, the liquid surface is formed such that it is concavely curved in the direction of the channel cross-section and a predetermined trough-shaped path for the small micro-mechanical part results, and at the end of the channel which closes the channel in the transport direction, a channel end wall is provided. Additionally, at the level of the liquid surface and in the extension of the predetermined path of the micromechanical part, an opening is provided in the channel end wall, an electromagnet or a permanent magnet is arranged outside the channel at a distance behind the opening of the channel end wall, and a stop for the micro-mechanical part is provided between the opening and the electromagnet or permanent magnet.

In this embodiment, the micro-mechanical part is spatially aligned on account of the curvature of the liquid surface in the channel section transverse to the channel direction in an analogous manner to that described with respect to the channel in the transport process. Means by which the spatial position of the micro-mechanical part can be definitively defined are provided in the form of the stop. The micro-mechanical part, which must consist of a magnetic material for positioning with this apparatus, is drawn by the electromagnetic through the opening and against the stop and stays there in a defined position. So that the micro-mechanical part can transported through the opening without difficulty, it is advantageous to provide the opening at the side of the channel end wall facing the channel interior with an inlet which widens in the direction towards the channel. As a result of such an inlet, the micro-mechanical part in the channel can be drawn more easily by the electromagnet into the opening from the liquid surface in the channel.

A further aspect of the invention consists of an apparatus for transporting and positioning micro-mechanical parts and comprises of a basin filled with liquid, a platform floating on the liquid surface in the basin on account of hydrostatic buoyancy and/or surface tension, and means for subjecting the platform to external forces in order to move the platform on the liquid surface, wherein a positioning basin is formed in the platform for receiving the micro-mechanical part, the positioning basin bounding a liquid surface, the proportions of which substantially correspond to those of the small micro-mechanical part and the geometrical dimensions of which are only slightly greater than those of the micro-mechanical part so that, before placement of the micro-mechanical part, and on account of adhesion and cohesion forces between the liquid, the edges of the positioning basin and the medium above the liquid, a concavely curved liquid surface is formed at least at the edges of the positioning basin.

The micro-mechanical part is positioned within the platform in the positioning basin in a similar manner as previously described in connection with the channel section having two channel end walls or an area bound on the liquid surface by a boundary member. Thus, the micro-mechanical part is positioned with respect to the surrounding platform when the platform is transported in the basin by being subjected to external forces, the micro-mechanical part in the positioning basin of the platform is transported in a corresponding manner. Thus, the platform can also be activated by mechanical contact without the danger of damage or plastic deformation of the micro-mechanical part occurring, as it is protected within the positioning basin by the liquid which surrounds it. When the platform, which can be more easily handled on account of its larger dimensions in comparison to the micro-mechanical part, is positioned, one has automatically also positioned the micro-mechanical part as it is in a defined position with respect to the platform.

Preferably, the means for exerting external forces on the platform consist of a synchronously linear motor, the stator of which defines the path of the platform on the surface of the liquid by means of its longitudinal extension and is arranged adjacent to the desired path, and the rotor of which linear motor is formed by at least a magnetic part of the platform. As the rotor is formed by a magnetic part of the platform or by a completely magnetic platform, a micro-mechanical part consisting of non-magnetic material can also be transported and positioned by means of this apparatus.

A preferred embodiment of the platform consists of the positioning basin within the platform bounding a partial surface of the liquid surface of the basin in which the platform floats. In a further useful embodiment of the platform, the positioning basin is formed within the platform as a closed bath wetted with liquid. In the first case, the platform corresponds to the boundary member, and the positioning basin corresponds to the bound area described in terms of the previously defined inventive positioning process. In the second case, a closed bath is provided on the platform, the liquid of which is separated from the liquid in the basin within which the platform floats. The platform corresponds to the channel section with two channel end walls previously described with respect to the positioning process. In this embodiment, the platform can therefore be removed from the basin together with the micro-mechanical part, which is not possible in the first embodiment, as the micro-mechanical part would remain in the basin in this case.

The platform can, for example, be formed as a plate, but can also take on any other desirable shapes which are useful for handling the platform.

The described inventive transport and positioning processes can be combined in various ways with one another. Normally, following transport of a micro-mechanical part, the positioning thereof is necessary. For example, the micro-mechanical part must either be removed from the liquid for a further operational step or a further step must be carried out on the liquid surface.

For example, the previously described positioning apparatus in which the micro-mechanical part is drawn from the liquid surface through an opening by means of an electromagnet and positioned at a stop is connected at the end of a transport channel or a transport lane as have also been described above.

A further possibility of combining an inventive transport apparatus with an inventive positioning apparatus consists of forming a channel section in a transport channel in such a manner that it is rotatable within a liquid-tight frame about its vertical plane axis and can be rotated into a position in which the channel section is closed at both ends by means of the frame. In this manner, a positioning apparatus is formed and the micro-mechanical manufactured part can, for example, be subjected in this stable position to a quality control with the aid of an optical measuring device.

The described positioning apparatus can also be used independently of the transport apparatus. For example, the micro-mechanical part can be placed in a positioning basin so that it positions itself on the curved liquid surface, a operational step can then be carried out and the part may then be removed again.

In the described inventive transport process and the associated apparatus, a plurality of micro-mechanical parts can be simultaneously transported in a channel or a transport lane arranged successively in a row. By joining several channels or several transport lanes together, a very flexible transport system can be realized. Positioning stations at which finishing processes are carried out can be integrated into such a system so that a substantially automatic handling of micro-mechanical parts during the production process can be realized. In the case of the breakdown of a machine at which a certain operational step is to be carried out, the following micro-mechanical parts can be diverted via diversion channels or lanes. In contrast, the production through-put of the micro-mechanical parts in commonly known mechanical gripping arrangements which are guided along a fixed rail is blocked when an operating station breaks down while, in the case of the commonly known handling methods for micro-mechanical parts, a very high proportion of rejects occurs during the manufacturing process because the manufactured parts break or plastically deform during handling, the inventive transport and positioning processes leads to uncomplicated, cost-effective and safe handling of micro-mechanical parts. Furthermore, in comparison to commonly known processes, the flexibility of the inventive processes is increased.

On account of the inventive platform for transporting and positioning micro-mechanical parts, additional handling possibilities are provided. The micro-mechanical part is protected within the platform, it is positioned with respect to the platform and the platform itself can be relatively easily transported and positioned, even manually.

The above-mentioned "slightly greater area" for the embodiments, e.g. employing a basin, would be a function of the shape of the part, the chosen geometrical shape of the boundary walls, and the materials chosen for the liquid, basin, and the medium above the liquid.

Examples of the maximum thickness of plates, foils or the like transportable over distilled water by the present invention include aluminum plate 1 mm thick and steel plate 0.2 mm thick.

In the following, the inventive process and apparatus are described in more detail with respect to exemplified embodiments shown in the figures.

Figure 1A:
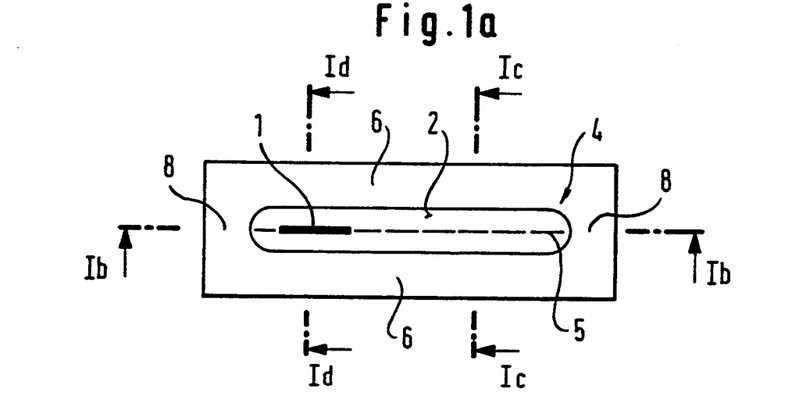
FIG. 1a shows a channel in plan view with a synchronous linear motor for transporting micro-mechanical parts.

FIG. 1a shows a transport channel 4 which is wetted by a liquid 3, on the surface 2 of which a micro-mechanical manufactured part 1 is placed. The predetermined path 5 of the micro-mechanical part 1 along which it is transported in the channel is shown in dotted lines. The channel is limited along the transport direction by side walls 6 and at the end of the transport path by channel end walls 8.

Figure 1B:
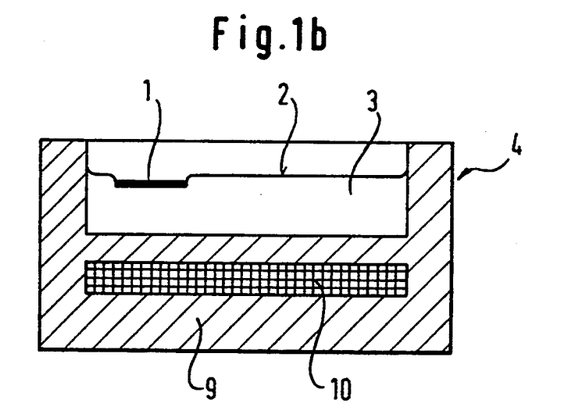

As can be seen in FIG. 1b, the small micro-mechanical part 1 is maintained on the liquid surface 2 on account of the surface tension of the liquid 3. A stator 10 is provided in the channel base 9, the stator extending along the predetermined path 5 and being part of a synchronous linear motor. The small micro-mechanical part 1 is premagnitized and acts as the rotor of the synchronous linear motor. On account of the electromagnetic field of the linear motor, electromagnetic forces act on the small micro-mechanical part in order to move it along its transport path.

Figure 1C:
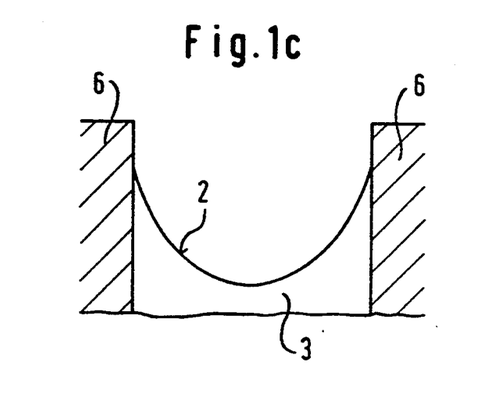
Figure 1D:
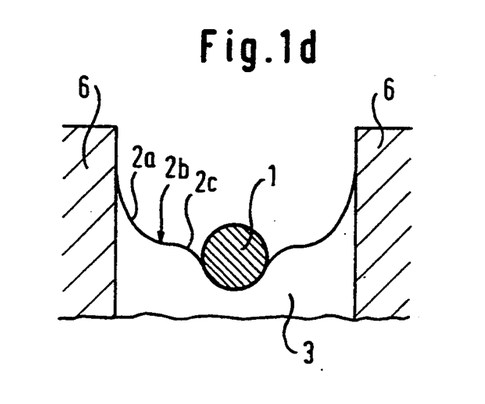
FIG. 1d shows a cross-sectional view (Id—Id) of the channel according to FIG. 1a with oblong micro-mechanical parts placed on the liquid surface.

The cross-section through the channel according to FIG. 1c shows how the liquid surface 2 is bent on account of the adhesion and cohesion forces between the liquid 3, the channel walls 6 and the surrounding atmosphere. In the example shown, a concave curvature of the liquid surface 2 is created in the transverse direction of the channel. Following placement of a micro-mechanical part, the geometry of the liquid surface 2 shown in FIG. 1d is created. In the transverse direction of the channel, a concave curvature 2a is present at the channel side walls 6 and, after a turning point 2b, the surface then has a convex curvature 2e in the region of the micro-mechanical part 1. As the channel 4 has a symmetrical cross-section and the inclination of the channel side walls 6 is the same, the micro-mechanical part is stabilized in the center of the channel. This ensues from the fact that the liquid surface 2 has a tendency to form a minimal surface. Thus, in the example of FIGS. 1a to 1d, a path along the central line of the channel is predefined for the micro-mechanical part. By means of the synchronous linear motor, the transport force acts to push the micro-mechanical part along this path. The shown part is an oblong manufactured part as, for example, a micro-surgical needle.

Figure 2A:
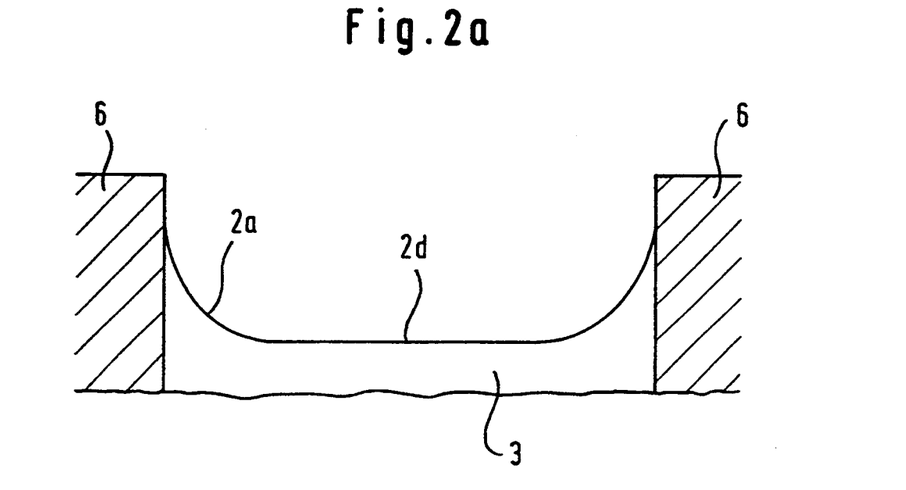
FIG. 2a shows a cross-sectional view of a channel for transporting micro-mechanical parts.
Figure 2B:
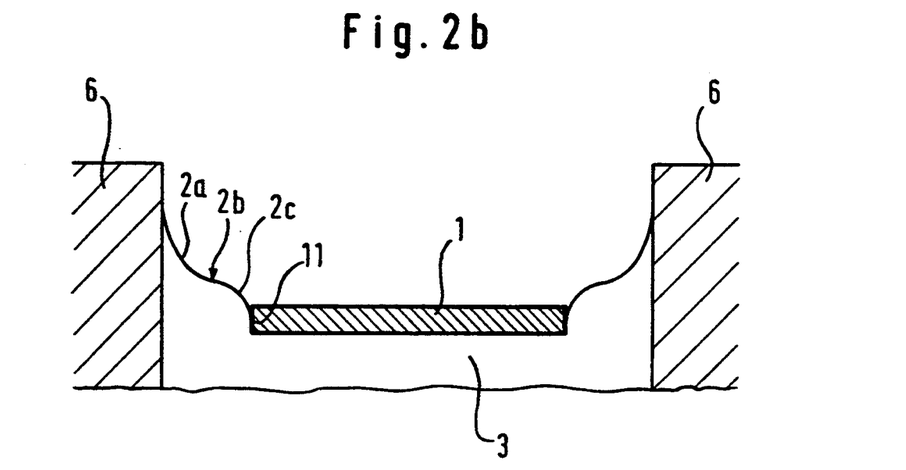
FIG. 2b shows a cross-sectional view of the channel according to FIG. 2a with planar micro-mechanical parts placed on the liquid surface.

FIG. 2a shows the cross-section of a wider channel than that shown in FIG. 1a to 1d. In this case, a concave curvature 2a of the liquid surface is only present in the area of the channel side walls 6, while a flat liquid surface 2d is present in the center of the channel. In FIG. 2b, a planar micro-mechanical part 1 is placed on the channel cross-section according to FIG. 2a, the part being carried by the surface tension. Preceeding from the channel side wall 6 towards the longitudinal edge 11 of the micro-mechanical part, a varying geometry of the liquid surface is created, from a concave curvature 2a via a turning point 2b to a convex curvature 2c. The planar micro-mechanical part adopts a stable position between the channel side walls 6.

On account of the geometry of the liquid surface according to FIGS. 1d and 2b which form due to the adhesion and cohesion forces, a striking of a micromechanical part 1 against the channel side wall 6 is prevented. The part is therefore protected by the surrounding liquid 3 during transport in the channel.

Figure 3A:
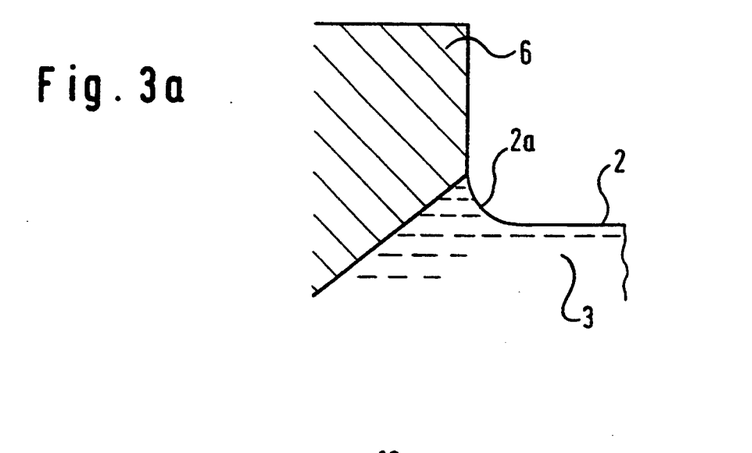
FIG. 3a shows an embodiment of a channel side wall in cross-section.
Figure 3B:
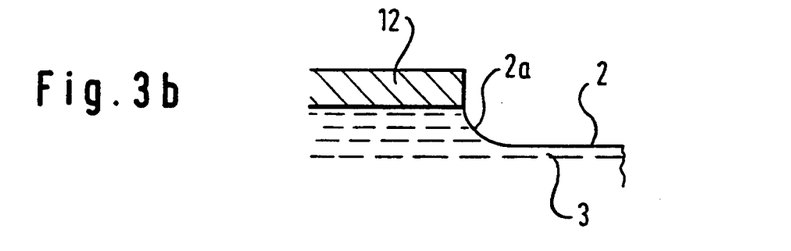
FIG. 3b shows an embodiment of a boundary member in cross-section.

The geometric cross-sectional shape of the channel can be varied in a simple manner. In addition to rectangular channel cross-sections, round or polygonal cross-sectional shapes can also be used. FIG. 3a shows a channel side wall 6 which, in connection with a vertical wall section, is angled outwardly in the lower region, a concave curvature 2a of the liquid surface forming at the edge. FIG. 3b shows a plate-like boundary member 12 which is arranged directly on the liquid surface 2. At the transition between the edge of the plate 12 and the free liquid surface, the liquid surface also bends concavely.

Figure 4A:
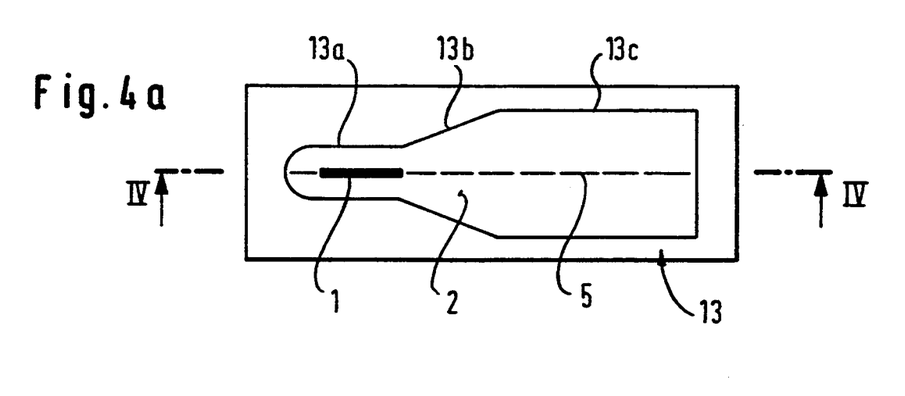
FIG. 4a shows a channel in plan view with a gradient along the liquid surface for transporting micro-mechanical parts.
Figure 4B:
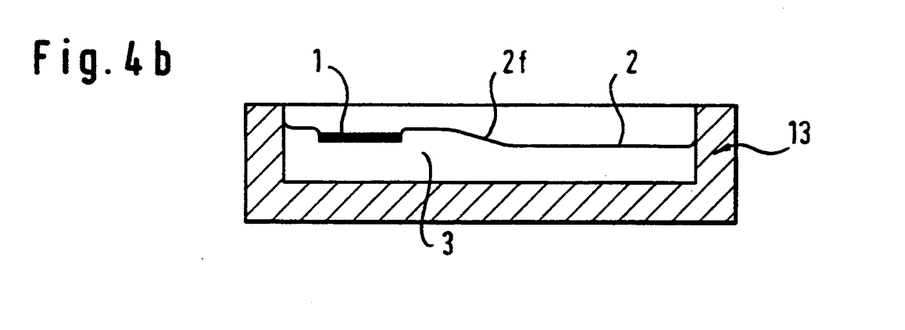
FIG. 4b shows a channel according to FIG. 4a in longitudinal cross-section (IV—IV)

In FIG. 4a, a transport channel 13 is shown in which the channel width changes in the transport direction from a narrower channel section 13a to a wider channel section 13c. The narrower channel section 13a and the wider channel section 13c are connected by a channel section 13b which widens in the transport direction. In the transverse direction of the channel, a concave surface curvature according to FIG. 1c is created before placement of the micro-mechanical part. The curvature in the channel section 13a is greater than the curvature in the channel section 13c. Thus, between these two channel sections, a gradient 2f occurs along the widening channel section 13b. This grandient 2f is shown in FIG. 4b. A part placed on the liquid surface is accelerated along the gradient by the driving force of the incline and proceeds further along its predetermined path in the channel section 13c. One thus has a transport system for micro-mechanical parts for short distances. The micro-mechanical part moves along its transport path in a stable manner between the channel side walls also in this case.

Figure 5A:
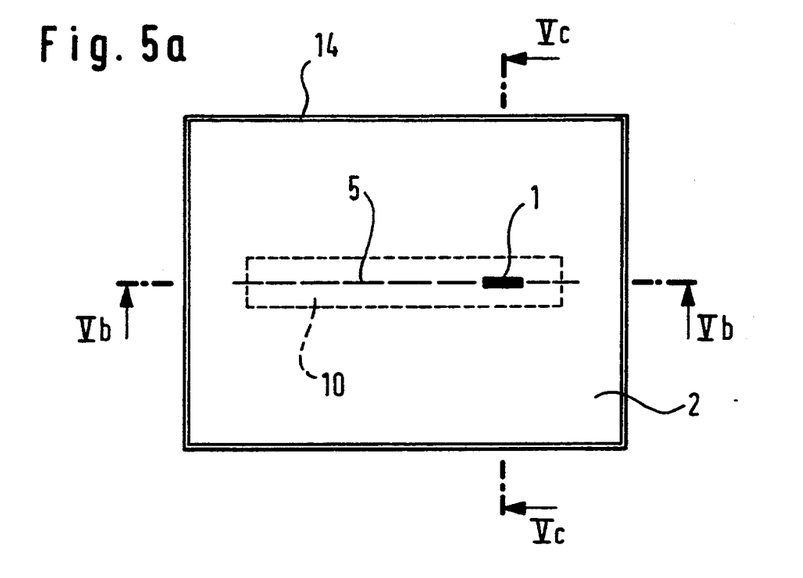
FIG. 5a shows a basin in plan view with a linear motor for transporting micro-mechanical parts.
Figure 5B:
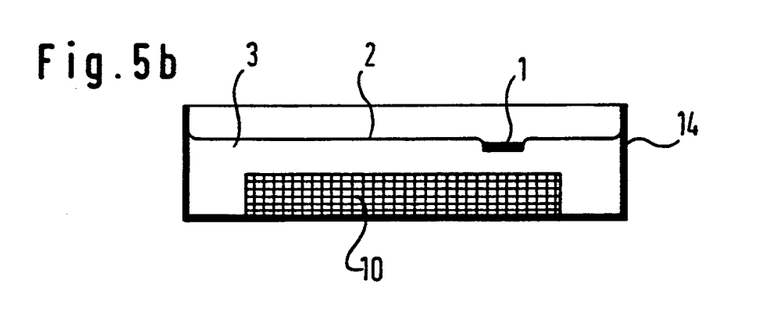
FIG. 5b shows a basin according to FIG. 5a in longitudinal section (Vb—Vb)
Figure 5C:
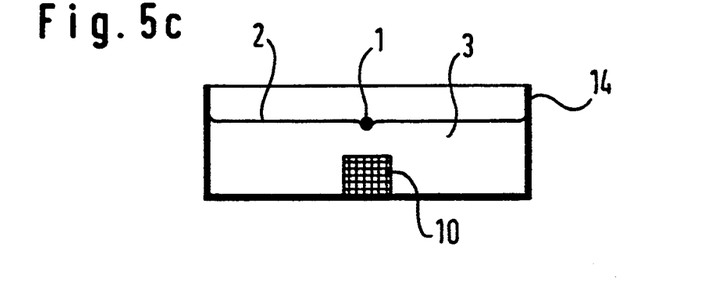
FIG. 5c shows a basin according to FIG. 5a in cross-section (Vc—Vc)

In FIG. 5a to 5c, a basin 14 filled with liquid 3 is shown, the liquid surface 2 of which is flat. A stator 10 is provided in the liquid of the basin, the stator being part of a synchronous linear motor. The premagnitized micro-mechanical part placed on the liquid surface acts as the rotor of the linear motor. On account of the extension of the stator 10 along the basin base, the path for the micro-mechanical part is predefined on the liquid surface above the stator. The part placed on the liquid surface therefore follows the extension of the stator. The micro-mechanical part is not stabilized on the flat liquid surface in terms of its angular orientation, but it is held on account of the electromagnetic forces of the synchronous motor on the predetermined path and transported along this. Several synchronous linear motors can be arranged in a single liquid basin 14 and several predetermined paths 5 for a part can be connected with one another in this manner.

Figure 6A:
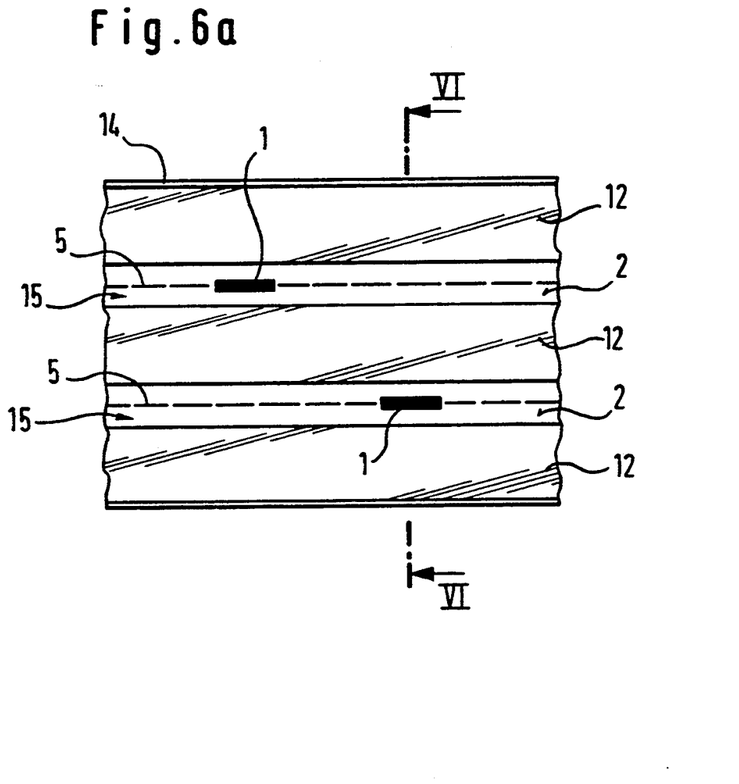
FIG. 6a shows a basin in plan view with boundary member and a linear motor for the transport of micro-mechanical parts.
Figure 6B:
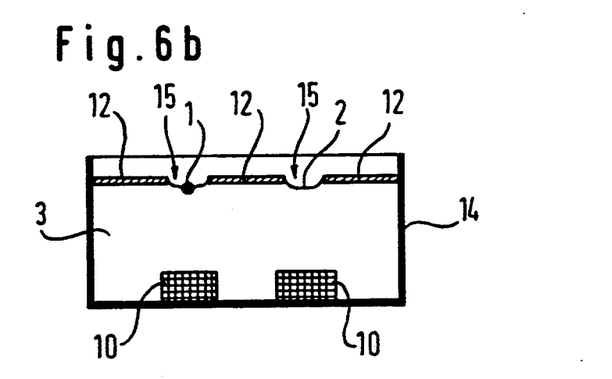
FIG. 6b shows a basin according to FIG. 6a in cross-section (VI—VI)

FIG. 6a shows a basin 14 filled with liquid, boundary member 12 being arranged on the liquid surface. These members in the form of plates 12 are arranged at a distance from one another such that individual transport lanes 15 are created. Stators 10 of synchronous linear motors are respectively arranged to follow the transport lanes 15 beneath the predetermined paths 5 of parts, as can be seen in FIG. 6b. As FIG. 6b also shows, the geometry of the liquid surface in the transport lanes 15 are created respectively analogously to FIG. 1d (left-hand transport lane with a micro-mechanical part) and FIG. 1c (right-hand transport lane without a part).

Figure 7A:
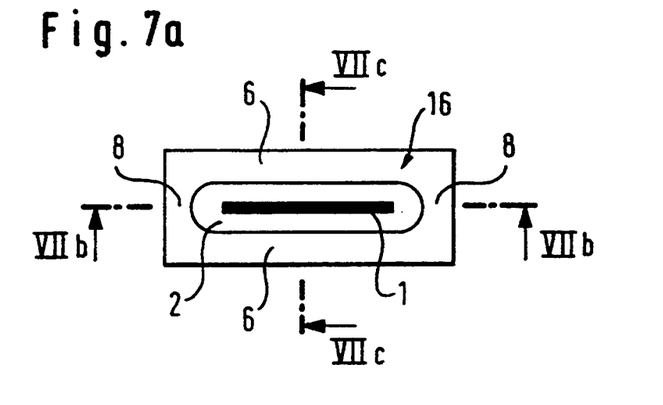
FIG. 7a shows a channel section for positioning micro-mechanical parts in plan view.
Figure 7B:
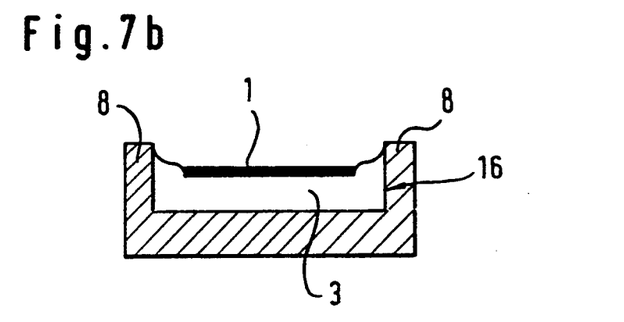
FIG. 7b shows a channel section according to FIG. 7a in longitudinal section (VIIb—VIIb)
Figure 7C:
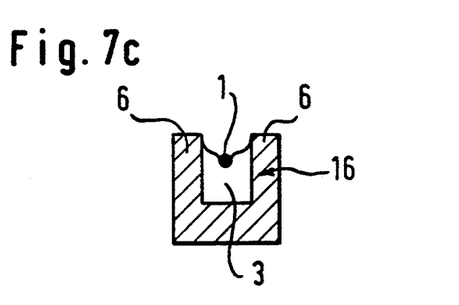
FIG. 7c shows a channel section according to FIG. 7a in cross-section (VIIc—VIIc)

An embodiment of an apparatus for positioning small micro-mechanical parts is shown in FIG. 7a to 7c. A channel section 16 with two channel end walls 8 corresponds in its proportions to the small micro-mechanical part 1 to be positioned. The dimensions of the liquid surface 2 in the channel are only slightly greater than the dimensions of the manufactured part 1. As can be seen in FIG. 7b and 7c, the micro-mechanical part positions itself in the liquid 3 on account of the geometry of the liquid surface which is created between the channel walls and the part on account of adhesion and cohesion forces as well as the gravitational force of the part. The part positions independently itself and lies in a stable position in which the surface of the liquid is minimized.

Figure 8:
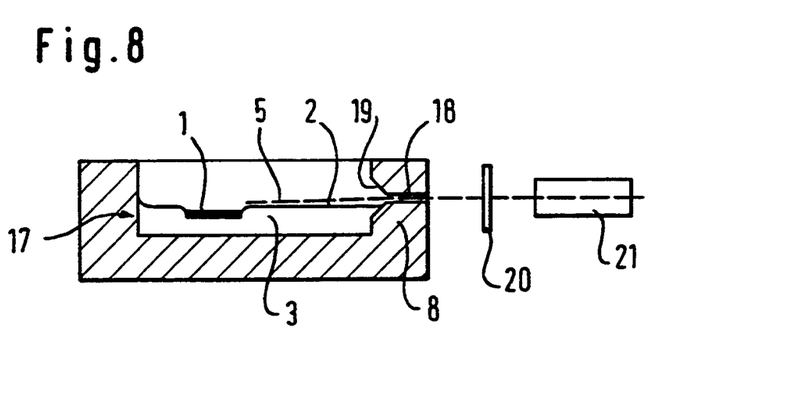
FIG. 8 shows an apparatus for positioning micro-mechanical parts with an electromagnet and a stop.

FIG. 8 shows a further embodiment of an apparatus for positioning a micro-mechanical part. A channel section 17 is provided, an opening 18 with a conical inlet 19 being arranged at the one end of the channel section 17 in the channel end wall 8. The opening 18 is located at the level of the liquid surface 2 in the channel and lies in the extension of the predetermined transport path of the micro-mechanical part 1. Also in the extension of this transport path are, outside the channel, a stop 20 as well an electromagnet 21. A micro-mechanical part 1 of magnetic material placed on the liquid surface is attracted by the attraction force of the electromagnet 21 along a path 5 on the liquid surface, enters through the conical inlet 19 in the opening 18, is then drawn off the liquid surface and finally strikes the stop 20 against which it is held by the electromagnetic attraction force. As this part passes the opening 18 at the end of the path 5, it has a defined spatial orientation and adopts a fixed position at the stop. Following the exact positioning of the part at the stop 20, an operational step can be carried out, for example the treatment of a micro-surgical needle with a laser. Should the micro-mechanical part not consist of magnetic material, but be premagnetized, it is also predefined which of its ends is attracted by the electromagnet. The inlet 19 simplifies the entry of the part from the liquid surface into the opening 18.

Figure 9A:
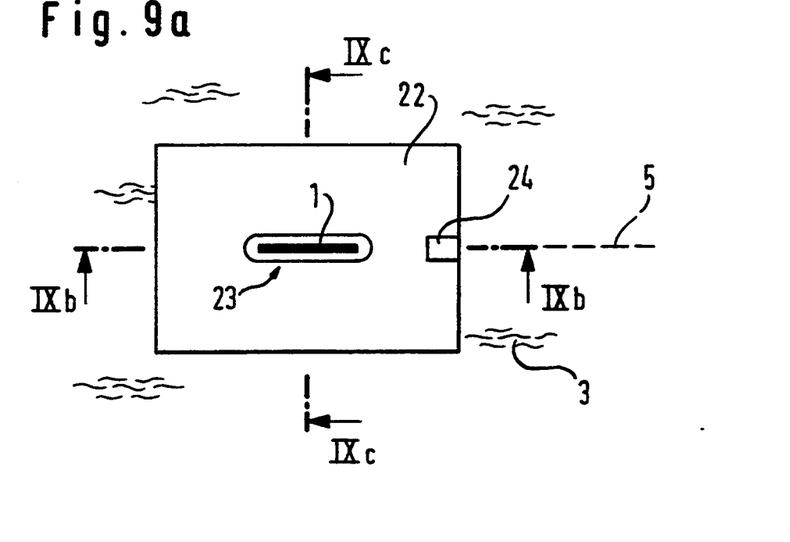
FIG. 9a shows an apparatus for transporting an positioning micro-mechanical parts in cross-section comprising a platform and a synchronous linear motor.
Figure 9B:
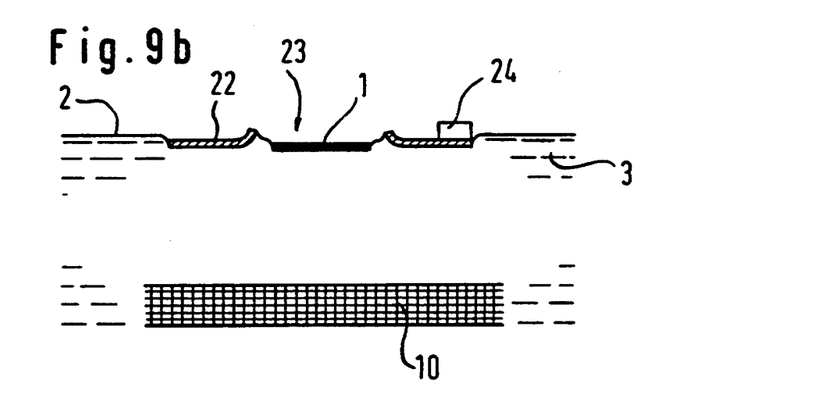
FIG. 9b shows an apparatus according to FIG. 9a in longitudinal cross-section (IXb—IXb)
Figure 9C:
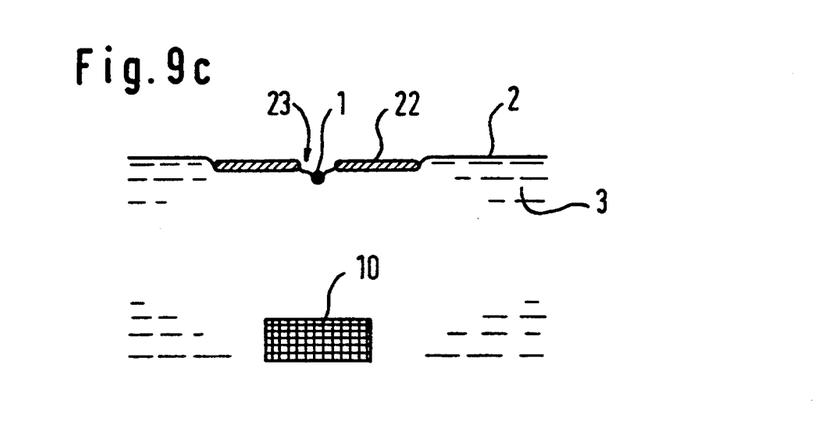
FIG. 9c shows an apparatus according to FIG. 9a in cross-section (IXc—IXc)

FIGS. 9a to 9c show an apparatus for transporting and positioning a micro-mechanical part. The apparatus includes a basin filled with liquid 3, a platform 22 and a synchronous linear motor. The platform 22 floats on the basin liquid on account of hydrostatic boyancy and/or surface tension. An opening to the surface of the liquid 3 in the basin is provided in the center of the platform 22. This opening serves as a positioning basin 23 for the small micro-mechanical part 1 to be transported and positioned. As can be seen in FIGS. 9b and 9c, the small micro-mechanical part positions itself in a stable position in an analogous manner to that described with respect to FIGS. 7a to 7c. The bending of the liquid surface between the edges of the positioning basin and the micro-mechanical part in the basin can be improved by appropriate geometrical shaping of the edges. As FIG. 9b shows, the platform edges at the positioning basin are curved upwardly. As already described, the micro-mechanical part positions itself in a stable location within the positioning basin in which the liquid surface between the part and the edges of the positioning basin is minimized. The platform is provided with a magnetic part 24 which acts as the rotor of the synchronous linear motor. As shown in FIGS. 9b and 9c, the associated stator 10 is placed in the liquid 3 of the basin and, on account of its longitudinal extension, defines the transport path 5 for the platform 22, and therefore also for the micro-mechanical part 1. The stator can equally be placed beneath the liquid 3, i.e. beneath the basin. The part 1 to be conveyed can therefore also be of a non-magnetic material, as the platform adopts the function of the rotor of the synchronous linear motor. The part 1 is continuously positioned with respect to the platform 22 during transport. For positioning the micro-mechanical part 1, for example to carry out a manufacturing step, it is sufficient to therefore position the platform 22 surrounding it. This can, for example, occur in that the platform 22 is introduced into a channel, the width of which corresponds to the width of the platform and that a defined stop for the platform is provided in the channel which determines the desired position for the operational step. By a corresponding design of the edges of the positioning basin 23 of the platform 22, namely, for example, by means of a displacement in height of two opposing edges, the micro-mechanical part can also, for example, adopt a tilted position. As an alternative to a rectangular shape, the platform 22 can naturally also have any other desired contour and means can be provided on the platform for the handling thereof.

Figure 10A:
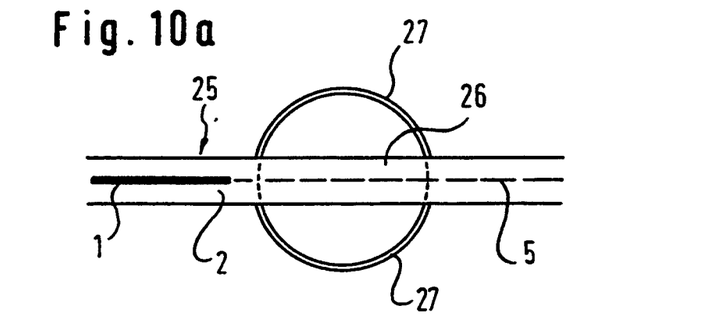
FIG. 10a shows a positioning apparatus integrated into a transport channel in plan view in the transport position.
Figure 10B:
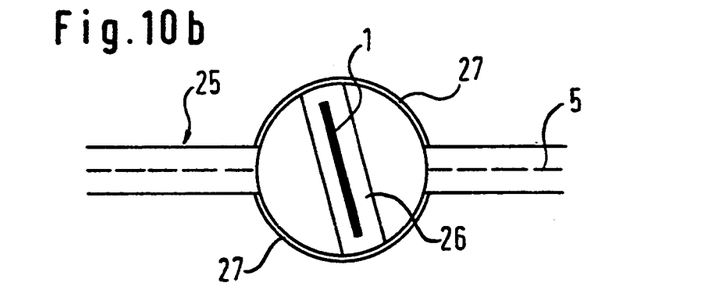
FIG. 10b shows an apparatus according to FIG. 10a in plan view in the positioning position.

FIG. 10a shows a transport channel 25 as described, for example, in connection with FIGS. 1a to 1d or FIGS. 4a and 4b. A channel section 26 is cut out of the transport channel 25 and is, for example, rotatable about its vertical axis by means of a motor (not shown). The rotation of this channel section 26 ensues within semicircular liquid-tight boundary walls 27 which prevent the liquid in the channel section 26 from flowing out of the channel section when the rotation occurs. In FIG. 10a, the transport position of the channel section 26 is shown in which the section is aligned parallel to the transport channel 25 and a micro-mechanical part 1 on the liquid surface of the channel can thus be transported through the positioning apparatus along a predetermined path 5. When the micro-mechanical part 1 is located in the channel section 26, this can be rotated, as shown in FIG. 10b, so that a closed positioning basin as shown in FIGS. 7a to 7c is provided. As described above, the micro-mechanical part positions itself under the influence of gravitation within the channel section 26 bounded by the boundary walls 27. A manufacturing step can be carried out for the defined position of the part and the part can subsequently again be transported in the transport channel 25, following rotation of the channel section 26, back into the transport position. The transport force can, for example, be exerted on the part by means of a synchronous linear motor.

Figure 11A:
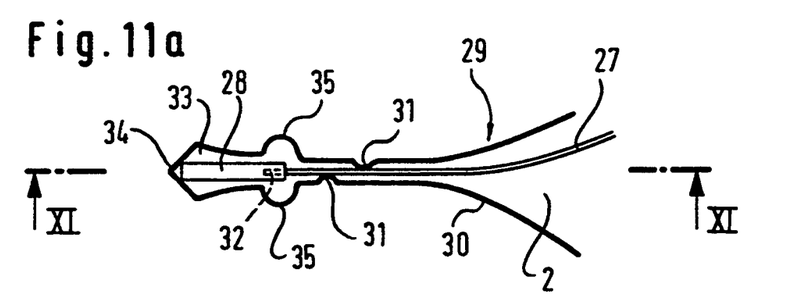
FIG. 11a shows an apparatus for threading a micro-mechanical-surgical thread into a micro-surgical needle in plan view.
Figure 11B:
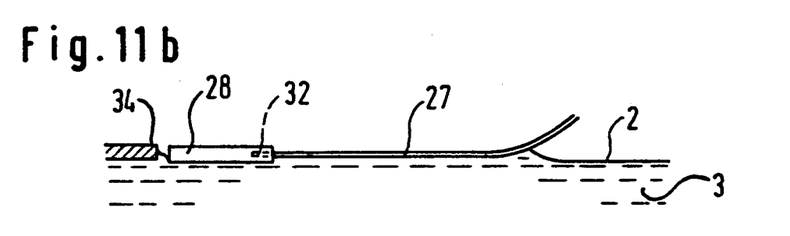
FIG. 11b shows an apparatus according to FIG. 11a in longitudinal section (XI—XI).

With reference to FIGS. 11a and 11b, an apparatus for threading a micro-surgical thread 27 into a micro-surgical needle 28 is described in the following. The micro-surgical needle 28 is positioned at the end of a channel 29 filled with liquid 3 which can also be arranged in a platform as described in connection with FIGS. 9a to 9c. The liquid surface 2 serves as the reference level for the needle and the thread. The thread is led through the conical inlet opening 30 of the channel 29 and then aligned by means of respectively displaced aligning protrusions 31 such that the forward end of the thread is flush with the needle opening 32 of the prepositioned needle. The micro-surgical needle 28 is held in a defined position in a positioning basin 23 on the liquid surface and in meeting with the forward end of the micro-surgical thread 27 in the opening 32 of the needle, is pressed against a stop 34. The position of the micro-surgical needle is predefined by this stop. When the thread is introduced into the opening 32 of the needle 28 with its forward end, the connecting position between the needle and the thread is consolidated by means of a connecting tool, e.g. "squashed", so that the thread remains securely fastened to the needle. In order to be able to apply the connecting tool, recesses 25 are arranged beside the position, during the threading step, of the connecting location between the needle and thread. On account of the fact that the micro-surgical needle 28 as well as the micro-surgical thread 27 are both held on the surface of a liquid, they are not exposed to any mechanical loads during the threading step which normally occur in the case of commonly known mechanical gripping means, and damage or plastic deformation of the micro-mechanical needle is therefore avoided. The geometric shape of the channel with the inlet 30 and the aligning protrusions 31 as well as a positioning basin 33 ensure that the thread reliably enters the opening 32 of the needle. This apparatus considerably reduces the time required for threading the thread into the needle and subsequently making the connection thereof, as both steps take place at the same location and the thread is safely led to the opening. Thus, the quantity of rejects on account of damage or deformation of the needle is considerably reduced.

I claim:

1. A method of transporting small micro-mechanical parts comprising the steps of placing a small micro-mechanical part on the surface of a still liquid and holding said part on the liquid surface on account of the surface tension of the liquid, such that a predetermined path is formed, subjecting the small micro-mechanical part to at least one external force, and transporting the small micro-mechanical part along the predetermined path on the surface of the liquid by means of the external force.

2. The method according to claim 1, wherein the external force by which the small micro-mechanical part is transported along the predetermined path is electromagnetic forces.

3. The method according to claim 1, wherein the external force by which the small micro-mechanical part is transported along the predetermined path is gravity.

4. The method according the claim 1, wherein the external force by which the small micro-mechanical part is transported along the predetermined path is aerodynamic forces.

5. An apparatus for transporting small micromechanical parts by placing a small micro-mechanical part on the surface of a still liquid transporting the small micro-mechanical part along a predetermined path on the surface of the liquid by means of an external force, comprising: means for holding said part on the liquid surface on account of the surface tension of the liquid, such that the predetermined path is formed, means for subjecting the small micro-mechanical part to the external force, a channel, wherein
   (a) the walls of the channel are wetted by a liquid,
   (b) the channel has a channel width which is greater than the width of the small micro-mechanical part, and
   (c) the channel has such a channel cross-sectional geometry and such an amount of liquid in the channel that, before placement of the small micromechanical part, and on account of adhesion and cohesion forces between the liquid, the channel walls and a medium above the liquid, the liquid surface is formed such that it is concavely curved at the edges of the channel in the direction of the channel cross section and a predetermined path for the small micro-mechanical part results.

6. The apparatus of claim 5, wherein the small micromechanical parts are oblong and the predetermined path is trough-shaped and before placement of the small micro-mechanical part the liquid surface is concavely curved in the direction of the channel cross-section.

7. The apparatus of claim 5, wherein the small micromechanical parts are flat and before placement of the small micro-mechanical part the liquid surface is flat in the center of the channel.

8. An apparatus for transporting small micromechanical parts by placing a small micro-mechanical part on the surface of a still liquid and transporting the small micro-mechanical part along a predetermined transport path on the surface of the liquid by means of at least one external force, comprising means for holding said part on the surface of the liquid on account of the surface tension of the liquid, such that the predetermined path is formed, means for subjecting the small micro-mechanical part to the external force, boundary members arranged in a basin filled with liquid at a distance from one another on the surface of the liquid, the boundary members bounding at least one transport path on the liquid surface, wherein
   (a) the width of the transport path is greater than the width of the small micro-mechanical part, and
   (b) the width of the transport path is selected and the geometry of the edges of the boundary members bounding the transport path is of a shape such that, before placement of the small micro-mechanical part, and on account of adhesion and cohesion forces between the liquid, the edges of the boundary members and a medium above the liquid, the surface of the liquid is formed such that it is concavely curved at the edges of the boundary members in the direction of the transport path cross-section and a predetermined path for the small micromechanical part results.

9. The apparatus of claim 8, wherein the small micromechanical part is oblong and the predetermined path is trough-shaped and, before placement of the small micro-mechanical part, the surface of the liquid is concavely curved.

10. The apparatus of claim 8, wherein the small micro-mechanical part is flat and the predetermined path is trough-shaped.

11. The apparatus of claim 10, wherein the center of the surface of the liquid of the predetermined path is flat before placement of the small micro-mechanical part.

12. The apparatus according to claim 5, wherein the means for purposefully subjecting the small micromechanical part to the external force includes a synchronous linear motor,
   (a) the stator of which is arranged adjacent the predetermined path such that the stator follows the predetermined path in its longitudinal extension, and
   (b) the rotor of which is formed by the small micromechanical part placed on the liquid surface respectively in the channel or the transport path.

13. The apparatus according to claim 8, wherein the means for purposefully subjecting the small micromechanical part to the external force includes a synchronous linear motor,
   (a) the stator of which is arranged adjacent the predetermined path such that the stator follows the predetermined path in its longitudinal extension, and (b) the rotor of which is formed by the small micro-mechanical part placed on the liquid surface respectively in the channel or the transport path.

14. The apparatus according to claim 5, wherein the small micro-mechanical part is premagnetized.

15. The apparatus according to claim 12, wherein the stator is arranged beneath the predetermined path in the base of the channel.

16. The apparatus according to claim 5, wherein the means for purposefully subjecting the small micro-mechanical part to external force comprises an airstream generator effective in the transport direction of the small micro-mechanical part.

17. The apparatus according to claim 13, wherein the stator is arranged beneath the predetermined path in the base of the channel.

18. The apparatus of claim 5, wherein before placement of the small micro-mechanical part the liquid surface is concavely curved in the direction of the channel cross-section and the predetermined path is trough-shaped, and the channel width increases in the transport direction at least in one channel section along the predetermined path.

19. An apparatus for transporting small micro-mechanical parts by placing the small micro-mechanical part on the surface of a still liquid, and transporting the small micro-mechanical part along a predetermined path on the surface of the liquid by means of at least one external force, comprising:
means for holding said part on the liquid surface on account of the surface tension of the liquid, such that a predetermined path is formed,
means for subjecting the small micro-mechanical part to at least one external force,
a basin, which is adapted to be filled with the liquid, such liquid having a flat liquid surface, and
a synchronous linear motor wherein
(a) the stator of the synchronous linear motor is arranged beneath and parallel to the liquid surface and the direction of the path of the small micro-mechanical part on the liquid surface above the stator is defined by the direction of longitudinal extension of the stator, and
(b) the rotor of the synchronous motor is formed by the small micro-mechanical part placed on the liquid surface in the basin.

20. A method of positioning a small micro-mechanical part, comprising the steps of,
placing the micro-mechanical part on a liquid surface,
holding the part on the liquid surface on account of the surface tension of the liquid surface, definitively aligning the small micro-mechanical part in terms of its spatial orientation on account of the geometry of the liquid surface, and setting the spatial position of the small micro-mechanical part.

21. An apparatus for positioning a small micro-mechanical part by placing the micro-mechanical part on a liquid surface, comprising:
means for holding the part on the liquid surface on account of the surface tension of the liquid surface, wherein the geometry of the liquid surface is adapted such that the small micro-mechanical part is definitively aligned in terms of its spatial orientation, and means for setting the spatial position of the small micro-mechanical part, comprising a channel section which is limited in its longitudinal dimension by means of two channel end walls, wherein (a) the proportions of the channel section substantially correspond to the proportions of the small micro-mechanical part to be positioned,
(b) the geometrical dimensions of the channel section are only slightly greater than the dimensions of the small micro-mechanical part, and
(c) the channel section includes such an amount of liquid that, before placement of the small micro-mechanical part, and on account of adhesion and cohesion forces between the liquid, the channel walls and the medium above the liquid, the liquid surface is concavely curved at the channel walls.

22. The apparatus of claim 21, wherein the small micro-mechanical parts are oblong and the liquid surface is concavely curved before placement of the small micro-mechanical part and the geometric dimensions are at most about 25% greater than the dimensions of the small micro-mechanical part.

23. The apparatus of claim 21, wherein the small micro-mechanical parts are flat and before placement of the small micro-mechanical part the liquid surface is flat in the middle of the channel and the geometric dimensions are at most about 25% greater than the dimensions of the small micro-mechanical part.

24. An apparatus for positioning a small micro-mechanical part by placing the micro-mechanical part on a liquid surface, comprising:
means for holding the part there on account of the surface tension of the liquid surface, wherein the geometry of the liquid surface is formed in such a manner that the small micro-mechanical part is definitively aligned in terms of its spatial orientation, and means for setting the spatial position of the small micro-mechanical part, wherein a boundary member is arranged in a basin, adapted to be filled with the liquid, on the surface of the liquid and bounds an area of the liquid surface, wherein
(a) the proportions of the area substantially corresponds to the small micro-mechanical part to be positioned,
(b) the geometric dimensions of the area are only slightly greater than those of the small micro-mechanical part, and
(c) the edges of the boundary member are shaped such that, before placement of the small micro-mechanical part, and on account of adhesion and cohesion forces between the liquid, the edges of the boundary member and the medium above the liquid, the liquid surface is formed in such a manner that it is concavely curved at the edges of the boundary member.

25. The apparatus of claim 24, wherein the small micro-mechanical parts are oblong and before placement of the small micro-mechanical part the liquid surface is concavely curved and the geometric dimensions are at most about 25% greater than the dimensions of the small micro-mechanical part.

26. The apparatus of claim 24, wherein the small micro-mechanical parts are flat and before placement of the small micro-mechanical part the liquid surface is flat in the middle of the area on the liquid surface and the geometric dimensions are at most about 25% greater than the dimensions of the small micro-mechanical part.

27. An apparatus for positioning a small micro-mechanical part by placing the micro-mechanical part on a liquid surface, comprising:
means for holding the part on the liquid surface on account of the surface tension of the liquid surface, wherein the geometry of the liquid surface is formed in such a manner that the small micro-mechanical part is definitively aligned in terms of its spatial orientation, and means for setting the spatial position of the small micro-mechanical part comprising a channel, wherein (a) the walls of the channel are wetted with a liquid, and (b) the channel has a channel width which is greater than the width of the small micro-mechanical part, and (c) the channel has such a channel cross-sectional geometry and such an amount of liquid in the channel that, before placement of the small micro-mechanical part, and on account of adhesion and cohesion forces between the liquid, the channel walls and the medium above the liquid, the liquid surface is formed such that it is concavely curved in the direction of the channel cross-section and a predetermined trough-shaped path for the small micro-mechanical part results, (d) a channel end wall is provided at the end of the channel which closes the channel in the transport direction, (e) an opening is provided in the channel end wall approximately at the level of the liquid surface and in the extension of the predetermined path of the small micro-mechanical part, (f) an opening is provided in the channel end wall approximately at the level of the liquid surface and in the extension of the predetermined path of the small micro-mechanical part, (g) an electromagnet or permanent magnet is arranged outside the channel at a distance behind the opening of the channel end wall, and (h) a stop for the small micro-mechanical part is provided between the opening and the electromagnet or permanent magnet.

28. The apparatus according to claim 27, wherein the opening has an inlet at the side of the channel end wall facing the channel interior which widens in the direction towards the channel.

29. An apparatus for transporting and for positioning small micro-mechanical parts, including (a) a basin filled with liquid, (b) a platform floating on the liquid surface in the basin on account at least one member of the group consisting of hydrostatic buoyancy and surface tension, and (c) means for subjecting the platform to external forces, (d) wherein a positioning basin is formed in the platform for receiving the small micro-mechanical part, the positioning basin bounding a liquid surface, the proportions of the liquid surface substantially correspond to those of the small micro-mechanical part and the geometric dimensions of the liquid surface are only slightly greater than those of the small micro-mechanical part so that, before placement of the small micro-mechanical part, and on account of adhesion and cohesion forces between the liquid, the edges of the positioning basin and a medium above the liquid, a concavely curved liquid surface is formed at least at the edges of the positioning basin.

30. The apparatus according to claim 29, wherein the means for subjecting the platform to external forces include a synchronous linear motor, (a) the stator of the motor defines the path of the platform on the surface of the liquid by means of its longitudinal extension and is arranged adjacent to the desired path, and (b) the rotor of the motor is formed by at least a magnetic part of the platform.

31. The apparatus according to claim 29, characterized in that the positioning basin in the platform bounds a partial surface of the liquid surface of the basin within which the platform floats and the geometric dimensions are at most about 25% greater than those of the small micro-mechanical part.

32. The apparatus according to claim 29, characterized in that the positioning basin is formed within the platform as a closed bath wetted with liquid.

* * * * *